United States Patent
Fidler et al.

(10) Patent No.: US 8,617,906 B2
(45) Date of Patent: Dec. 31, 2013

(54) IDENTIFICATION AND SCREENING OF TRIPTOLIDE TARGET MOLECULES

(75) Inventors: John M. Fidler, Oakland, CA (US); John H. Musser, San Carlos, CA (US)

(73) Assignee: Pharmagenesis, Inc., Redwood City, CA (US)

( * ) Notice: Subject to any disclaimer, the term of this patent is extended or adjusted under 35 U.S.C. 154(b) by 1071 days.

(21) Appl. No.: 11/665,177

(22) PCT Filed: Oct. 12, 2005

(86) PCT No.: PCT/US2005/036751
§ 371 (c)(1),
(2), (4) Date: Nov. 8, 2007

(87) PCT Pub. No.: WO2006/044496
PCT Pub. Date: Apr. 27, 2006

(65) Prior Publication Data
US 2008/0193948 A1 Aug. 14, 2008

Related U.S. Application Data

(60) Provisional application No. 60/618,290, filed on Oct. 13, 2004.

(51) Int. Cl.
*G01N 33/566* (2006.01)
*G01N 33/567* (2006.01)
*C07D 307/77* (2006.01)
*A01N 43/00* (2006.01)

(52) U.S. Cl.
USPC ........... 436/501; 436/503; 549/297; 549/298; 514/183

(58) Field of Classification Search
None
See application file for complete search history.

(56) References Cited

U.S. PATENT DOCUMENTS

| | | | |
|---|---|---|---|
| 4,005,108 A | 1/1977 | Kupchan et al. | |
| 5,192,817 A | 3/1993 | Takaishi et al. | |
| 5,294,443 A | 3/1994 | Lipsky et al. | |
| 5,430,054 A | 7/1995 | Qian et al. | |
| 5,468,772 A | 11/1995 | Xu et al. | |
| 5,580,562 A | 12/1996 | Lipsky et al. | |
| 5,648,376 A | 7/1997 | Strobel et al. | |
| 5,663,335 A | 9/1997 | Qi et al. | |
| 5,759,550 A | 6/1998 | Weidmann et al. | |
| 5,843,452 A | 12/1998 | Wiedmann et al. | |
| 5,919,816 A | 7/1999 | Hausheer et al. | |
| 5,962,516 A | 10/1999 | Qi et al. | |
| 5,972,998 A | 10/1999 | Jung et al. | |
| 6,004,999 A | 12/1999 | Jung et al. | |
| 6,011,042 A | 1/2000 | Greenwald et al. | |
| 6,103,875 A | 8/2000 | Martinez-Miller et al. | |
| 6,150,539 A | 11/2000 | Musser | |
| 6,294,546 B1 | 9/2001 | Rosen et al. | |
| 6,329,148 B1 | 12/2001 | Rosen et al. | |
| 6,458,537 B1 | 10/2002 | Staub et al. | |
| 6,537,984 B2 | 3/2003 | Rosen et al. | |
| 6,548,537 B1 | 4/2003 | Dai et al. | |
| 6,569,893 B2 | 5/2003 | Dai et al. | |
| 6,579,720 B1 | 6/2003 | Pidgeon et al. | |
| 6,599,499 B1 | 7/2003 | Rosen et al. | |
| 6,620,843 B2 | 9/2003 | Fidler et al. | |
| 6,777,441 B2 | 8/2004 | Wang et al. | |
| 6,943,259 B2 | 9/2005 | Dai et al. | |
| 7,019,151 B2 | 3/2006 | Dai et al. | |
| 7,098,348 B2 | 8/2006 | Dai et al. | |
| 7,417,069 B2 | 8/2008 | Dai et al. | |
| 7,847,109 B2 * | 12/2010 | Dai et al. ...................... | 549/297 |
| 2002/0077350 A1 | 6/2002 | Babish et al. | |
| 2002/0099051 A1 | 7/2002 | Fidler et al. | |
| 2004/0018260 A1 | 1/2004 | Ren et al. | |
| 2004/0152767 A1 | 8/2004 | Dai et al. | |
| 2004/0198808 A1 | 10/2004 | Dai et al. | |
| 2004/0235943 A1 | 11/2004 | Dai et al. | |
| 2005/0288364 A1 | 12/2005 | Dai et al. | |
| 2007/0244080 A1 | 10/2007 | Fidler et al. | |
| 2007/0249048 A1 | 10/2007 | Dai et al. | |
| 2007/0282114 A1 | 12/2007 | An et al. | |
| 2008/0287530 A1 | 11/2008 | Yuan et al. | |

FOREIGN PATENT DOCUMENTS

| | | |
|---|---|---|
| CN | 1052859 A | 7/1991 |
| CN | 1317248 A | 10/2001 |
| EP | 0 156 643 B1 | 10/1985 |
| JP | 03 178977 | 8/1991 |
| WO | WO 94/26265 A1 | 11/1994 |
| WO | WO 95/13082 A1 | 5/1995 |
| WO | WO 98/52933 A1 | 11/1998 |
| WO | WO 98/52951 A1 | 11/1998 |
| WO | WO 00/12483 A1 | 3/2000 |
| WO | WO 00/63212 A1 | 10/2000 |
| WO | WO 02/17931 A1 | 3/2002 |

(Continued)

OTHER PUBLICATIONS

Lee et al. (1999), JBC, vol. 274 (19), pp. 13451-13455.*
The International Search Report and Written Opinion for PCT application PCT/US2005/036751, search report dated Jul. 1, 2008, 12 pages (2008).
Kupchan et al., "Triptolide and tripdiolide, novel antileukemic diterpenoid triepoxides from *Tripterygium wilfordii*", *American Chemical Society*, 94(20):7194-7195 (1972).
Aumuller, G., C. Schulze and C. Viebahn, *Microsc. Res. Tech.*, 20:50-72(1992).
Becker et al., *Eur. J. Biochem.*, 267:6118-6125 (2000).

(Continued)

*Primary Examiner* — Christine J Saoud
*Assistant Examiner* — Jegatheesan Seharaseyon
(74) *Attorney, Agent, or Firm* — Susan J. Myers Fitch; McDermott Will & Emery LLP

(57) ABSTRACT

The identification of triptolide target molecules is described. Also described are methods of screening triptolide-related compounds for binding to these molecules, including screening for enhanced and/or selective binding, and expression analysis of the target molecules in normal and in diseased tissue.

2 Claims, No Drawings

(56) References Cited

FOREIGN PATENT DOCUMENTS

| | | |
|---|---|---|
| WO | WO 02/070472 A1 | 9/2002 |
| WO | WO 02/074759 A1 | 9/2002 |
| WO | WO 03/101951 A2 | 12/2003 |
| WO | WO 2005/000291 A1 | 1/2005 |
| WO | WO 2005/020887 A | 3/2005 |
| WO | WO 2005/062913 A2 | 7/2005 |
| WO | WO 2005/084365 A2 | 9/2005 |
| WO | WO 2006/012204 A2 | 2/2006 |

OTHER PUBLICATIONS

Berg, D., C. Holzmann and O. Reiss, Nature Rev. Neurosci. 4:752-62 (2003).
Britton et al., *J. Nat. Prod.*, 66:838-43 (2003).
Chang, W.T. et al., *J. Biol. Chem.*, 276:2221-7 (2001).
Chen et al., *Transplantation*, 73:115 (2002).
Chen et al.,*Transplantation*, 70(10):1442-1447 (2000).
Cheng, X.X. et al., Yao Xue Xue Bao, 37:339-342 (2002).
Fidler et al., *Transplantation*, 74:445-457 (2002).
Fidler et al., *Mol. Cancer Ther.*, 2(9):855-62 (2003).
Fruman et al., *Ann. Rev. Biochem.*, 67:481-507 (1998).
Fu et al., *Ann. Rev. PharmacoL Toxicol.*, 40:617-47 (2000).
Gabbiani, G., *J. Pathol.*, 200:500-3 (2003).
Garcia et al., *Biochimie*, 85:721-6 (2003).
Gilles et al., *Cancer Res.*, 63:2658-64 (2003).
Gleichmann et al., *Immunol. Today*, 5:324 (1984).
Goto et al., *Cell Tissue Res.*, 315:209-21 (2004).
Gross et al., *N. Engl. J. Med.*, 345(7):517-525 (2001).
He, Q. et al., *Beijing Da Xue Xue Bao*, 35:252-5 (Jun. 2003).
Jerums et al. *Arch. Biochem. Biophys.*, 419:55-62 (2003).
Jones et al. *Proc. Natl. Acad. Sci. USA*, 95:9331-6 (1998).
Kershenobich et al., *Annals of. Hepatol.*, 2(4):159-63 (2003).
Korngold, B. and J. Sprent, *J. Exp. Med.*, 148:1687-98 (1978).
Kurz et al., *J Biol. Chem.*, 275(18): 1394813954 (2000).
Larribere et al., *Cell Death Differ.*, 11:1084-1091 (2004).
Leonard et al., *Journal of Heart and Lung Transplantation*, 21(12):1314-1318 (2002).
Li et al., *Exp. Neurol.*, 179:28-37 (2003).
Li et al., *J. Neuroimmunol.*, 148:24-31 (2004).
Lin et al., *DNA Cell Biol.*, 19(1):1-7 (2000).
List et al., *Exp Hematol.*, 32:526-35 (2004).
Lowell et al. *Free Rad. Biol. Med.*, 28:418-27 (2000).
Lundstrom et al., *J. Biol. Chem.*, 267(13): 9047-9052 (1992).
Mason et al., *Am. J. Respir. Crit. Care Med.* 160:1771-1777 1999.
Masters et al., *J. Biol Chem.*, 276(48):45193-45200 (2001).
Mesa et al., *Leukemia*, 17:849-55 (2003).
Ming et al., *Sheng Li Xue Bao*, 56:73-8 (2004).
Murase et al., *Transplantation*, 55(4):701-708 (1993).
Ono and Lindsey, *J. Thor. Cardiovasc. Surg.*, 57(2):225-29 (1969).
Ory, et al., *Curr Biol.*, 13:1356-64 (2003).
Otsuka et al., *Biochem Biophys Res Commun.*, 289:876-81 (2001).
Pei et al. *Am J Pathol.*, 163(3):845-58 (2003).
Powis, G. and W. R. Montfort, *Ann.Rev. Pharmacol. Toxicol.*, 41:261-95 (2000).
Qiu et al., *J. of Biol. Chem.*, 274(19):13443-13450 (1999).
Qiu et al., *Drugs R&D*, 4(1):1-18 (2003).
Redpath et al., *EMBO J.*, 15:2291-7 (1996).
Sato et al., *Proc Natl Acad Sci USA*, 97(20):10832-7 (2000).
Schlesinger et al., *Annals of Diagnostics Pathology.* 2(5):321-34 (1998).
Schlesinger et al., *Curr Opin Pulm Med.* 4:288-293 (1998).
Schwaller et al., *J Biol Chem.*, 278(9):7154-7159 (2003).
Selman et al. *Ann. Intern. Med.*, 134:136-151 (2001).
Shevchenko et al., *Proc Natl Acad Sci USA*, 93:14440-14445 (1996).
Shevchenko et al., *Anal. Chem.*, 68(5):850-858 (1996).
Show et al., *Endocrinology.* 144(12):5530-6 (2003).
Solit et al., *Semin Oncol.*, 30(5):709-16 (2003).
Sontag et al., , *EMBO J.*, 16(18):5662-71 (1997).
Tolstonog et al., *DNA Cell Biol.*, 20(9):509-29(2001).

Wang, J. and Morris, R.E., *Transplantation Proc.*, 23(1):699-702 (1991).
Wang et al., *Transplantation*, 70(3):447-455 (2000).
Wang et al., *J Pediatr Surg.*, 37(4):648-52 (2002).
Whitesell et al., *Curr Cancer Drug Targets.* 3: 349-358 (2003).
Yamagishi et al., *Kidney Int.*, 63:464-473 (2003).
Yang et al., *Cancer Res.*, 61:4010-4016 (2001).
Yano, H. et al., *J. Biol. Chem.*, 268(34):25846-25856 (1993).
Yuan et al., *OsteoArthritis and Cartilage*, 12:38-45 (2004).
Zhou et al., *Neuroreport* , 14(7):1091-5 (2003).
Zhou, Y.X. et al., *Ai Zheng* 21:1108-8 (2002).
Anderson, Wayne K. et al., "Synthesis, Evaluation of Chemical Reactivity, and Murine Antineoplastic Activity of 2-Hydroxy-5-(3,4-dichlorophenyl)-6,7-bis(hydroxymethyl)-2,3-dihydro-1$H$-pyrrolizine Bis(2-propylcarbamate) and 2-Acyloxy Derivatives as Potential Water-Soluble Prodrugs[1]", *J. Med. Chem.*, 26:1333-1338 (1983).
Cheng et al., "Research on extraction technology of Tripterygium", *Chinese Journal of Pharmaceuticals*, 21(10):435-436 (No English translation) (1990).
Dan et al., "Studies on triepoxide analogs of triptolide", *Tetrahedron Letters*, 38(39):6865-6868 (1997).
De Groot Franciscus M. H. et al., "Synthesis and Biological Evaluation of 2'Carbamate-Linked and 2'-Carbonate-Linked Prodrugs of Paclitaxel: Selective Activation by the Tumor-Associated Protease Plasmin", *J. Med. Chem.*, 43:3093-3102 (2000).
De Quan Yu et al., "Chemical Transformation of Triptolide", *Chinese Chemical Letters*, 2(12):937-940 (1991).
Dittert, L.W. et al., "Acetaminophen Prodrugs I Synthesis, Physicochemical Properties, and Analgesic Activity", *Journal of Pharmaceutical Sciences*, 57(5):774-780 (1968).
Dittert, L.W. et al., "Acetaminophen Prodrugs II Effect of Structure and Enzyme Source on Enzymatic and Nonenzymatic Hydrolysis of Carbonate Esters", *Journal of Pharmaceutical Sciences*, 57(5):780-783 (1968).
Englebienne et al., *Drug Design Reviews-Online*, "The Place of Biosteric Sila Substitution in Drug Design", 2 pages (2005).
Hansen, Kristian T. et al., "Carbamate Ester Prodrus of Dopaminergic Compounds: Synthesis, Stability, and Bioconversion", *Journal of Pharmaceutical Sciences*, 80(8):793-798 (1991).
Hansen, Laila B. et al., "Ketobemidone prodrugs for buccal delivery", *Acta Pharm. Nord.*, 3(2):77-82 (1991).
Houtman, J.C. et al., "Early phosphorylation kinetics of proteins involved in proximal TCR-mediated signaling pathways",*Journal of Immunology*, 175(4):2449-2458 (2005)
Huang, Tien L. et al., "Hydrolysis of Carbonates, Thiocarbonates, Carbamates, and Carboxylic Esters of α-Naphthol, β-Naphthol, and ρ-Nitrophenol by Human, Rat, and Mouse Liver Carboxylesterases", *Pharmaceutical Research*, 10(5):639-648 (1993).
Jiang, X-H. et al., "Functional p53 is required for triptolide-induced apoptosis and AP-1 and nuclear factor-kappaB activation in gastric cancer cells",*Oncogene*, 20(55):8009-8018 (2001).
Jiarun, Z. et al., "Screening of active anti-inflammatory, immunosuppressive and antifertility components of *Tripterygium wilfordii*", ACTA Academiae Medicinae Sinicae 13(6):391-397 (English Abstract only) (1991).
Kahns, A. M. et al., "Prodrugs of Peptides. 18. Synthesis and Evaluation of Various Esters of Desmopressin (dDAVP)", *Pharmaceutical Research*, 10(1):68-74 (1993).
Keyser, F. D. et al., "The role of T cells in Rheumatoid Arthritis", *Clinical Rgeumatology*, 14(Suppl 2):5-9 (1995).
Khanna, A.K. and Mehta, M.R., "Targeted in vitro and in vivo gene transfer into T lymphocytes: potential of direct inhibition of alloimmune activation", *BMC Immunology*, 7(26):1-10 (2006).
Kutney, J.P. et al., "Studies with plant cell cultures of the Chinese herbal plant, *Tripterygium wilfordii*, Synthesis and biotransformation of diterpene analogues", *Heterocycles*, 44(1):2-11 (1997).
Leuenroth, S.J. and Crews, C.M., "Studies on calcium dependence reveal multiple modes of action for triptolide", *Chemistry and Biology*, 12(12):1259-1268 (2005).

(56) References Cited

OTHER PUBLICATIONS

Li, K.K. and Fidler, J.M., "PG490-88 erxerts 1-16 potent anticancer activity alone and in combination therapy in a nude mouse xenograft model", Proceedings of the American Association for Cancer Research Annual Meeting Mar. 2001, 42:73, Abstract #391 (2001).
Lundy, S.K. et al., "Cells of the synovium in rheumatoid arthritis", *Arthritis Research & Therapy*, 9(1):1-11 (2007).
Matlin, S.A. et al., "Male antifertility compounds from *Tripterygium wilfordi Hook F.*", *Contraception*, 47:387-400 (1993).
Gu, Ming et al., "Effect of Chinese herb *Tripterygium wilfordii* Hook F monomer triptolide on apoptosis of PC12 cells induced by Aβ1-42" *ACTA Physiologica Sinica*, 56(1):73-78 (2004) (English Abstract translation).
Nassar, M. N. et al., "Effects of Structural Variations on the Rates of Enzymatic and Nonenzymatic Hydrolysis of Carbonate and Carbamate Esters", *Journal of Pharmaceutical Sciences*, 81(3):295-298 (1992).
Ning, L. et al., "Biotransformation of triptolide by *Cunninghamella blakesleana*", Tetrahedron, 59(23):4209-4213 (2003).
Reichert, T.E. et al., "Interleukin-2 expression in human carcinoma cell lines and its role in cell cycle progression", *Oncogene*, 19(4):514-525 (2000).
Savolainen, Jouko et al., "Synthesis and in vitrolin vivo evaluation of novel oral *N*-alkyl- and *N,N*-dialkyl-carbamate esters of entacapone", *Life Sciences*, 67:205-216 (2000).
Shamon, L.A. et al., "Evaluation of the mutagenic, cytotoxic, and antitumor potential of triptolide, a highly oxygenated diterpene isolated from *Tripterygium wilfordii*", Cancer Letters, 112:113-117 (1997).
Shanmuganathan et al., "Enhanced brain delivery of an anti-HIV nucleoside 2'-F-ara-ddl by xanthine oxidase mediated biotransformation", *J. Med. Chem.*, 37:821-827 (1994).
Stella, V.J. et al., "Prodrugs, Do they have advantages in Clinical Practice ?", *Drugs*, 29:455-473 (1985).
Tunek, Anders et al., "Hydrolysis of ³H-Bambuterol, A Carbamate Prodrug of Terbutaline, in Blood from Humans and Laboratory Animals In Vitro", *Biochemical Pharmacology*, 37(20):3867-3876 (1988).
Van Tamelen et al., "Biogenetic-type total synthesis of (t, −) -triptonide and (.+−.)-triptolide", STN International Database, CAPLUS database Document No. 96:143107 2 pages (1982).

Vierling et al., "Highly fluorinated amphiphiles as drug and gene carrier and delivery systems", *Journal of Fluorine Chemistry*, 107:337-354 (2001).
Waller, D.G. and George, C.F., "Prodrugs", *Br. J. Clin. Pharmac.*, 28:497-507 (1989).
Wahlgren, C-F. et al, "Itch and inflammation induced by intradermally injected interleukin-2 in atopic dermatitis patients and healthy subjects", *Arch Dermatol Res.*, 287(6):572-580 (1995).
Wang, X. et al., "Mechanism of triptolide-induced apoptosis: Effect on caspase activation and Bid cleavage and essentiality of the hydroxyl group of triptolide", J. Mol. Med., 84:405-415 (2006).
Weibel, Helle et al., "Macromolecular prodrugs IXX. Kinetics of hydrolysis of benzyl dextran carbonate ester conjugates in aqueous buffer solutions and human plasma", *Acta Pharm. Nord.*, 3(3):159-162 (1991).
Weng, G. et al. "Advances in studies on apoptosis induced by *Tripterygium wilfordii*", *Chinese Traditional and Herbal Drugs*, 33(11):1053-1054 (2002) (No English Abstract Translation).
Yamamoto, R. et al., "Pharmaceutical Studies on water-Soluble corticosteroid derivatives I. Stability of Hydrocortisone 21 Hemiesters in Solution", Journal of the Pharmaceutical Society of Japan, 46(8):855-862 (1971).
Yang, S. et al., "Triptolide Induces apoptotic death of T lymphocyte", *Immunopharmacology*, 40:139-149 (1998).
Yang, S. et al., "Triptolide Inhibits the Growth and Metastasis of Solid Tumors", *Molecular Cancer Therapeutics*, 2:65-72 (2003).
Zhang et al., "Studies on Diterpenoids from leaves of *Tripterygium wilfordii*", ACTA Pharmaceutica Sinica, 28(2):110-115 (1993). (English Abstract translation).
Zheng et al., "Screening of active iantiinflammatory, immunosuppressive and antifertility components of *Tripterygium wilfordii*", Chemiacl Abstracts 117(9): Abstract No. 83085a (1992).
Chen, J-Y et al., "Improved Preparation of Triptolide Extract", *Chinese Journal of Pharmaceutcials*, 20(5):195 and 200 (Dec. 31, 1989) (English translation of abstract and concise explanation of relevance from Foreign Office Action).
Textbook of Chinese Medicine Chemistry for Chinese Colleges of Traditional Chinese Medicine in the New Century (for Chinese Medicine Specialty), Kuang Hai-Xue p. 23, Chinese Press of Traditional Chinese Medicine (Jun. 30, 2003) (English translation of abstract and concise explanation of relevance from Foreign Office Action).

\* cited by examiner

IDENTIFICATION AND SCREENING OF TRIPTOLIDE TARGET MOLECULES

CROSS REFERENCE TO RELATED APPLICATIONS

This application is a U.S. National Stage of International Patent Application No. PCT/US2005/036751, filed Oct. 12, 2005, which claims the benefit of U.S. Provisional Application No. 60/618,290, filed Oct. 13, 2004, each of which is hereby incorporated by reference in its entirety.

FIELD OF THE INVENTION

The invention relates to the use of triptolide target molecules, as identified herein, for screening of triptolide-related compounds for binding to these molecules, including enhanced and/or selective binding. The invention also relates to expression analysis of the target molecules in normal and in diseased tissue.

REFERENCES

Aumuller, G., C. Schulze and C. Viebahn, *Microsc. Res. Tech.* 20:50-72(1992).

Berg, D., C. Holzmann and O. Reiss, *Nature Rev. Neurosci.* 4: 752-62 (2003).

Besker, K, S. Gromer, R. H. Schirmer and S. Muller, *Eur. J. Biochem.* 267:6118-6125 (2000).

Britton, R., M. Roberge, C. Brown, R. van Soest and R. J. Andersen, *J. Nat. Prod.* 66:838-43 (2003).

Chang, W. T. et al., *J. Biol. Chem.* 276: 2221-7 (2001).

Cheng, X. X. et al., *Yao Xue Xue Bao* 37:339-42 (2002).

Fidler, J. M., K. Li, C. Chung, K. Wei, J. A. Ross, M. Gao, and G. D. Rosen, *Mol. Cancer Ther.* 2(9):855-62 (2003).

Fruman, D. A., R. E. Meyers and L. C. Cantley, *Ann. Rev. Biochem.* 67:481-507 (1998).

Fu, H., R. R. Subramanian and S. C. Masters, *Ann. Rev. Pharmacol. Toxicol.* 40:617-47 (2000).

Garcia, A., X. Cayla, J. Guergnon, F. Dessauge, V. Hospital, M. P. Rebollo, A. Fleischer and A. Rebollo, *Biochimie.* 85:721-6 (2003).

Gilles, C., M. Polette, M. Mestdagt, B. Nawrocki-Raby, P. Ruggeri, P. Birembaut and J. M. Foidait, *Cancer Res.* 63:2658-64 (2003).

Gleichmann, E. et al., *Immunol. Today* 5:324 (1984).

Gu, M. et al., *Sheng Li Xue Bao* 56:73-8 (2004).

He, Q. et al., *Beijing Da Xue Xue Bao* 35:252-5 (June 2003).

Jones, S. L., J. Wang, C. W. Turck and E. J. Brown, *Proc. Natl. Acad. Sci. USA* 95:9331-6 (1998).

Komgold, B. and J. Sprent, *J. Exp. Med.* 148:1687-98 (1978).

Kurz, E., K. B. Leader, D. J. Kroll M. Clark and F. Gieseler, "Modulation of human DNA topoisomerase II alpha function by interaction with 14-3-3 epsilon". *J. Biol. Chem.* 275: 13948 (2000).

Larribere, L. et al., *Cell Death Differ*, Epub (Jul. 9, 2004).

Li, F. Q. et al., *Exp. Neurol.* 179:28-37 (2003).

Li, F. Q. et al., *J. Neuroimmunol.* 148:24-31 (2004).

Lin, C. S. et al., "Upregulation of L-plastin gene by testosterone in breast and prostate cancer cells: identification of three cooperative androgen receptor-binding sequences". *DNA Cell Biol.* 19:1-7(2000).

List, A. F. et al., *Exp Hematol.* 32:526-35 (2004).

Lowell, M. A., X. Chengsong, S. P. Gabbita and W. R. Markesbery, *Free Rad. Biol. Med.* 28:418-27 (2000).

Lundstrom, J. et al., *J. Biol. Chem.* 267: 9047-9052 (1992).

Masters, S. C. and H. J. Fu, *Biol Chem* 276:45193-200 (2001).

Mesa, R. A. et al., "In vitro antiproliferative activity of the farnesyltransferase inhibitor R115777 in hematopoietic progenitors from patients with myelofibrosis with myeloid metaplasia". *Leukemia* 17:849-55 (2003).

Murase, N. et al., *Transplantation* 55:701 (1993).

Ono and Lindsey, *J. Thor. Cardiovasc. Surg.* 57:225-29 (1969).

Ory, S., M. Zhou, T. P. Conrads, T. D. Veenstra and D. K. Morrison, *Curr Biol.* 13:1356-64 (2003).

Otsuka, M, M. Kato, T. Yoshikawa, H. Chen, E. J. Brown, Y. Masuho, M. Omata and N. Seki, *Biochem Biophys Res Commun.* 289:876-81 (2001).

Pei, J. J., C. X. Gong, W. L. An, B. Winblad, R. F. Cowburn, I. Grundke-Iqbal and K. Iqbal, *Am J Pathol.* 163:845-58 (2003).

Powis, G. and W. R. Montfoil, *Ann. Rev. Pharmacol. Toxicol.* 41:261-95 (2000).

Redpath, N. T. et al., *EMBO J.* 15:2291-7 (1996).

Sato, S., N. Fujita and T. Tsuruo, *Proc Natl Acad Sci USA* 97:10832-7 (2000).

Schwaller M., B. Wilkinson and H. F. Gilbert, *J Biol Chem.* 278:7154-9 (2003).

Shevchenko, A. et al., "Mass spectrometric sequencing of proteins from silver-stained polyacrylamide gels". *Anal. Chem.* 68:850-858 (1996a).

Shevchenko, A. et al., "Linking genome and proteome by mass spectrometry: Large scale identification of yeast proteins from two-dimensional gels". *Proc Natl Acad Sci USA* 93:14440-14445 (1996b).

Show, M. D., M. D. Anway, J. S. Folmer and B. R. Zirkin, *Endocrinology.* 144:5530-6 (2003).

Solit, D. B., H. I. Scher and N. Rosen, *Semin Oncol.* 30:709-16 (2003).

Sontag, E., J. M. Sontag and A. Garcia, *EMBO J.* 16:5662-71 (1997).

Tolstonog, G. V., R. L. Shoeman, U. Traub and P. Traub. *DNA Cell Biol.* 20:509-29 (2001).

Wang, J. and Morris, R. E., *Transplantation Proc.* 23:699 (1991).

Wang, X. et al., PCT Pubn. No. WO 2002/17931 (2002a).

Wang, Z. Q., Y. Watanabe, A. Toki and T. Itano. Altered distribution of Seitoli cell vimentin and increased apoptosis in cryptorchid rats. *J Pediatr Surg.* 37:648-52 (2002b).

Whitesell, L., R. Bagatell and R. Falsey, *Curr Cancer Drug Targets.* 3: 349-58 (2003).

Yang, J., J. M. Yang, M. Iannone, W. J. Shib, Y. Lin and W. N. Hait, *Cancer Res.* 61:4010-6 (2001).

Yano, H. et al., *J. Biol. Chem.* 268:25846-56 (1993).

Yuan, G. H., M. Tanaka, K. Masuko-Hongo, A. Shibakawa, T. Kato, K. Nishioka and H. Nakamura, *Osteoarthritis Cartilage* 12:38-45 (2004).

Zhou, H. F. et al., *Neuroreport* 14:1091-5 (2003).

Zhou, Y. X. et al., *Ai Zheng* 21:1108-8 (October 2002).

BACKGROUND OF THE INVENTION

Triptolide, a compound derived from the Chinese medicinal plant *Tripterygium wilfordii* (TW), has been shown to have significant immunosuppressive activity, e.g. in the treatment of autoimmune disease, and in treating or preventing transplantation rejection, including the treatment of graft-versus-host disease (GVHD), a condition in which transplanted marrow cells attack the recipient's cells. Various prodrugs and other analogs of triptolide have also shown such activity. See, for example, U.S. Pat. Nos. 4,005,108, 5,294,443, 5,843,452, 5,648,376, and 5,962,516, which are incorporated herein by reference. Triptolide and its prodrugs and other analogs have also shown significant anticancer activity, including reduction of solid tumors in vivo. See, for example, co-owned U.S. Pat. No. 6,620,843, which is incorporated herein by reference, and Fidler et al., 2003.

SUMMARY OF THE INVENTION

In one aspect, the invention provides a method of screening a triptolide analog for biological activity, the method comprising:

determining the binding affinity of said triptolide analog to at least one triptolide target molecule, wherein said target molecule is any molecule selected from the group consisting of:

HSP 90 β (designated herein as PG771),
L-plastin (designated PG772),
14-3-3 ε (designated PG773),
Thioredoxin Reductase (designated PG774),
Protein Disulfide Isomerase (designated PG775),
Phosphatidyl Inositol 3 Kinase (Class II) (designated PG776),
Hypothetical Protein FLJ20297 (designated PG777),
Vimentin (designated PG778),
Eukaryotic Translation Elongation Factor 2 (EEF2) (designated PG786),
Hypothetical Protein GI 14758649 (designated PG787),
Hypothetical Protein GI 11277141 (designated PG788),
Human Serine/Threonine Protein Phosphatase 2A (130 KDa regulatory subunit PP2A) (designated PG789), and
Hypothetical Protein GI 7705346 (designated PG790).

The analog can be designated a "selectively binding" analog if its binding affinity to a given first target molecule differs from its binding affinity to a second target molecule by a factor of 10 or more.

Binding affinity of a triptolide analog to a triptolide target molecule can be correlated with a therapeutic activity associated with binding to that target molecule. For example, strong and/or selective binding to target molecule PG773 may be correlated with inhibition of progression of Alzheimer's or Parkinson's disease, as discussed further below.

In another aspect, the triptolide target molecules identified herein can be used to determine whether a disease state is amenable to treatment with triptolide or a triptolide analog, by (a) determining the level, state of activation, and/or cellular location of a triptolide target molecule, selected from the group listed above, in a cell or tissue sample in which the disease state is present; (b) determining the level, state of activation, and/or cellular location of the triptolide target molecule in a normal cell or tissue sample; and (c) selecting that disease state as amenable to treatment with triptolide or a triptolide analog, if the level, state of activation, and cellular location of the triptolide target molecule differs between the diseased sample and the normal sample.

For example, the target molecule may be present at a higher level (e.g. more highly expressed) in a diseased sample than in a normal sample. Alternatively, or in addition, it may be present in a different state of activation; that is, it may be phosphorylated, acylated, or truncated. Alternatively, or in addition, its cellular localization (e.g. nuclear vs. cytoplasmic) may be altered.

Such a process may be followed by administration of triptolide or a triptolide analog to the cell or tissue sample in which the disease state is present, and in which an altered level, form, and/or localization of a triptolide target molecule is observed. Preferably, the analog is one that shows enhanced and/or selective binding to the target molecule. Steps (a) and (b) can then be repeated, thereby determining if the triptolide or triptolide analog is effective to modulate or alleviate the disease state, by influencing the activity of the target molecule.

In another aspect, the target molecules may be used in a method of identifying a triptolide analog for use in combination therapy, by: (a) determining the binding affinity of the triptolide analog to a triptolide target molecule selected from the group listed above; (b) identifying at least one target molecule to which said analog binds preferentially, and (c) selecting said triptolide analog for use in combination therapy with a drug that binds to said target molecule or to a molecule that is in the same cellular signaling pathway as said target molecule.

Alternatively, such a method may comprise: (a) identifying a disease state in which the level, state of activation, and/or cellular location of a triptolide target molecule, selected from the group listed above, differs from that in a normal tissue; (b) identifying a triptolide analog that binds, preferably selectively, to that target molecule; and (c) selecting the triptolide analog for use in combination therapy with a drug that is known to modulate the disease state.

These and other objects and features of the invention will become more fully apparent in the following detailed description of the invention.

DETAILED DESCRIPTION OF THE INVENTION

I. Triptolide Target Molecules

A. Isolation and Identification

Molecular targets of triptolide were identified, as described in the Examples below, by isolation of compounds binding to tritium-labeled triptolide in Jurkat cell culture. Accordingly, targets relevant to anticancer activity and/or T cell immunity may be present. The target molecules that were identified include:

HSP 90β (designated herein as PG771),
L-plastin (designated PG772),
14-3-3 ε (designated PG773),
Thioredoxin Reductase (designated PG774),
Protein Disulfide Isomerase (designated PG775),
Phosphatidyl Inositol 3 Kinase (Class II) (designated PG776),
Hypothetical Protein FLJ20297 (see Genbank Acc. No. 060421) (designated PG777),
Vimentin (designated PG778),
Eukaryotic Translation Elongation Factor 2 (EEF2) (designated PG786),
Hypothetical Protein GI 14758649 (see Genbank Acc. No. XP 044844) (designated PG787),
Hypothetical Protein GI 11277141 (see Genbank Acc. No. T46243) (designated PG788),
Human Serine/Threonine Protein Phosphatase 2A (130 KDa regulatory subunit PP2A) (designated PG789), and
Hypothetical Protein GI 7705346 (see Genbank Acc. No. NP 057195) (designated PG790).

B. Properties of the Triptolide Binding Compounds

HSP 90β (PG771) is reported to bind to molecules in pathways involved in lymphocyte immune activation, such as the MAP kinase pathway. Serine/threonine kinase Akt is a downstream effector molecule of Phosphatidyl Inositol 3 Kinase and is thought to mediate many biological actions toward anti-apoptotic responses. Akt forms a complex with HSP 90 beta (PG771) in vivo, and inhibition of Akt-Hsp90 binding leads to the dephosphorylation and inactivation of Akt, which increases sensitivity of the cells to apoptosis-inducing stimulus (Sato et al., 2000). HSP 90β is also involved in accommodation to metabolic and environmental stress, which has implications for a variety of disease states including cancer. Modulation of the activity of HSP 90 proteins is recognized as a promising therapeutic approach in cancer treatment (Solit et al., 2003; Whitesell et al., 2003.

L-Plastin (PG772) is a leukocyte-specific actin-bundling protein that has been implicated in regulating polymorphonuclear neutrophil signal transduction (Jones et al., 1998).

14-3-3 ε (PG773) has shown associations with DNA topoisomerase, a molecular target of some anticancer agents. It is also highly expressed in neurological tissues and may be a target for second-generation triptolide analogs in neuroprotection. It is elevated in Alzheimer's disease and present in Lewy bodies in Parkinson's disease (Berg et al., 2003). PG773 is among a group of related molecules that, as a class, bind to and modulate the activities of a multitude of functionally diverse signaling proteins, interfere with an apoptosis checkpoint function (a possible link via p53 to p21), and modulate the intracellular localization of cell cycle regulatory molecules during phases of the cell cycle and in response to the DNA damage (a possible link to p53) (Fu et al., 2000). Finally, this protein class is known to interact with p53 and enhance p53 DNA-binding activity. Triptolide has been shown to modulate p53 and the p53 pathway, inhibiting the cell cycle arrest induced by p21 after p53 activation (Chang et al., 2001).

Thioredoxin reductase (PG774) reduces thioredoxin-1. An increased level of thioredoxin-1, which stimulates cell growth and is an inhibitor of apoptosis, is found in many aggressively growing human tumors. Thioredoxin-1 has several activities, including the regulation of transcription factor activity (Powis and Montfort, 2000). Thioredoxin reductase has links to critical components of cell metabolism and plays an important role in cell proliferation, including DNA synthesis and gene transcription (including AP-1 and NF-κb transcription factors). Triptolide is known to inhibit NF-κB activation and the transactivation of NF-κB-inducible genes.

Thioredoxin reductase is a target of auranofin, an antirheumatic drug used in treating rheumatoid arthritis, and it may play a pathophysiologic role in chronic diseases such as rheumatoid arthritis, Sjogren's syndrome, and cancer (Besker et al., 2000). Reduced thioredoxin synergizes with IL-1 and IL-2, suggesting a role for thioredoxin reductase in enhancing proliferation and responses in the immune system. Inhibition of thioredoxin reductase may exert anti-proliferative influence in tumor cells or in hyperstimulated and/or pathological immune responses.

The brains of Alzheimer's disease patients show increased thioredoxin reductase activity, possibly contributing to the enhanced oxidative stress and subsequent neurodegeneration (Lowell et al., 2000). Inhibition of thioredoxin may serve as a treatment for neurodegenerative diseases such as Alzheimer's disease.

Protein Disulfide Isomerase (PG775) catalyzes the formation of disulfides (oxidase activity) during oxidative protein folding, as well as the rearrangement of incorrect disulfide pairings (isomerase activity), accelerating both processes without drastically altering the refolding pathway (Schwaller et al., 2003). Involvement in proper protein folding and intramolecular bond formation suggest that protein disulfide isomerase could have relevance for a variety of conditions including cancer and neurodegeneration. Misfolded proteins are involved in neurological conditions such as Alzheimer's disease and Huntington's disease.

Phosphatidyl Inositol 3 Kinase (Class II) (PG776) is among a class of molecules considered to have a key role in intracellular signal transduction, both in immunity and in cancer (Fruman et al., 1998). This molecule feeds into several signaling and activation pathways that are important in a variety of conditions. The primary enzymatic activity of the P13-kinases is the phosphorylation of inositol lipids (phosphoinositides) on the 3-position of the inositol head group. Different members of the P13-kinase family generate different lipid products. Class II kinases can phosphorylate phosphatidyl inositol (PI) and PI(4)P. It appears that the class II kinases are activated by tyrosine kinase-coupled receptors.

Vimentin (PG778) is an intermediate filament expressed in various neoplasms, most strongly in those originating from mesenchymal cells. It is the only intermediate filament protein that deviates from tissue-specific and developmentally regulated pattern of expression. Cytoplasmic and nuclear redistribution of beta-catenin, and de novo expression of vimentin, are frequently involved in the epithelial to mesenchymal transition associated with increased invasive migratory properties of epithelial cells (Gilles et al., 2003), and vimentin is transactivated by beta-catenin in breast cancer cell lines. Vimentin may also fulfill a protective function against oxidative cell damage (Tolstonog et al., 2001). Vimentin displays affinity for, and forms cross linkage products with, recombinogenic nuclear as well as mitochondrial DNA in intact cells, and it may be involved in repairing DNA damage, a function that could enhance survival in cancer cells by counteracting the effects of chemotherapy. Recombinational events mediated by vimentin also appear to take place when cells pass through the genetically unstable state of crisis to attain immortality, a transition that is relevant for the oncogenic transformation and the development of more difficult to treat tumors.

Vimentin is used as a cytological marker for identification of Sertoli cells using immunohistochemistry, although Leydig cells, as well as a variety of epithelial cells, also express this protein. Sertoli cell vimentin filaments are important for maintaining the structural integrity of the seminiferous epithelium (Wang et al., 2002b). Vimentin, as a component of intermediate filaments, is involved in the compartmentation of the Sertoli cell into a perinuclear stable zone and a peripheral trafficking zone with fluctuating shape that is important with respect to the germ cell-supporting surface of the cell (Aumuller et al., 1992).

Eukaryotic Translation Elongation Factor 2 kinase, or EEF2 kinase (PG786) is markedly increased in several forms of malignancy. Nonspecific inhibitors of this enzyme and disruptors of its association with an appropriate chaperone protein promote tumor cell death (Yang et al., 2001).

Protein phosphorylation is probably the major regulatory mechanism employed by eukaryotic cells, and Human Serine/Threonine Protein Phosphatase 2A (130 KDa regulatory subunit PP2A) (designated PG789) is one of the major serine/threonine-specific protein phosphatases. One of the signaling targets of PG789 is the mitogen-activated protein kinase (MAPK/ERK) cascade. PG789 interacts with certain regulators of the Bcl-2 family in the control of apoptosis (Garcia et al., 2003). In Alzheimer's disease brain, the activity of PG789 is compromised, and that of the extracellular signal-regulated protein kinase (ERK1/2) of the mitogen-activated protein kinase (MAPK) family is up-regulated, possibly resulting in over-phosphorylation of target proteins (Pei et al., 2003). Modulation of PG789 activity may alter the balance of phosphorylation/dephosphorylation in a positive way.

PG789 positively regulates Ras signaling by dephosphorylating Kinase Suppressor of Ras (KSR) and Raf-1 on critical 14-3-3 binding sites (Ory et al., 2003). Inhibition of PG789 would suppress the Ras activation pathway, acting as a brake on activation and proliferation, possibly in cancer cells as well as overstimulated immune system cells (as in organ transplant rejection and autoimmune disease). PG789 also plays a major role in downregulation of the mitogen-activated protein (MAP) kinase pathway and is a key regulator of JNK in the context of inflammatory stimulus. Furthermore, PG789 plays a key role in the response of cells to growth factors and stress signals like TNF-alpha (Sontag et al., 1997).

Inhibitors of the G2 DNA damage checkpoint can selectively sensitize cancer cells with impaired p53 tumor suppressor activity to DNA-damaging drugs or ionizing radiation. Inhibitors of PG789 have been proposed to act in this way, and may enhance the efficacy of DNA damaging chemotherapeutic agents (Britton et al., 2003).

The above-described triptolide target molecules can be grouped into very general categories based on their expected binding targets and specificity. For example, target molecules having widespread binding activity include HSP 90β (PG771), Hypothetical Protein GI 14758649 similar to HSP 90β (PG787), Hypothetical Protein GI 11277141 superfamily HSP 90 (PG788), 14-3-3 ε (PG773), and Protein Disulfide Isomerase (PG775). Binding of a drug to these molecules is expected to disrupt signaling pathways critical to some diseases, such as cancer or certain autoimmune responses. Protein Disulfide Isomerase, in particular, is involved in proper protein folding and may have an effect on conditions in which misfolded proteins are involved, such as cancer or neurological conditions such as Alzheimer's disease and Huntington's disease. Targeting of molecules having widespread binding activity may be less selective and more prone to producing side effects than targeting of molecules having less widespread binding activity.

Another target molecule involved in protein folding and redox regulation is Thioredoxin Reductase (PG774), which stimulates growth, enhances proliferation, and possibly plays a role in cancer, Alzheimer's disease, and autoimmune diseases, e.g. rheumatoid arthritis.

Triptolide target molecules involved in signal transduction, and which are expected to have greater cell specificity than the widespread binding molecules noted above, include L-plastin (PG772), a structural, leukocyte-specific actin-bundling protein involved in signal transduction and involved in various cancers, Phosphatidyl Inositol 3 Kinase (Class II) (PG776), also involved in cancer and in immunity, and Thioredoxin Reductase (PG774).

Several other target molecules, in addition to those noted above, can be classified as relevant to cancer, and could be used, for example, in combination therapy with conventional chemotherapeutic agents. These include Eukaryotic Translation Elongation Factor 2 (PG786), which is associated with malignancy, and Human Serine/Threonine Protein Phosphatase 2A (PG789), one of the major serine/threonine-specific protein phosphatases. Inhibitors of the G2 DNA damage checkpoint can selectively sensitize cancer cells with impaired p53 tumor suppressor activity to killing by DNA-damaging drugs or ionizing radiation; certain inhibitors of Human Serine/Threonine Protein Phosphatase 2A (PG789) have been proposed to act in this way.

II. Triptolide Analogs

Triptolide analogs, as the term is used herein, include various structural modifications of the natural product triptolide (designated herein as PG490). They may include naturally occurring analogs, such as 2-hydroxytriptolide or 16-hydroxytriptolide (tripdiolide), although the term generally refers herein to synthetically prepared analogs. As used herein, the term "triptolide-related compounds" refers to triptolide and its analogs, and preferably refers to analogs.

Structural modifications may include, for example, ring opening of an epoxy or lactone ring of triptolide; conversion of a hydroxyl group (either naturally occurring or produced by such ring opening) to a carboxylic ester, inorganic ester (e.g. sulfonate), carbonate, or carbamate, to an aldehyde or ketone via oxidation, or to a hydrogen atom via subsequent reduction; conversion of a single bond to a double bond, and/or substitution of a hydrogen atom by a halogen, alkyl, alkenyl, hydroxyl, alkoxy, acyl, or amino group. Examples of triptolide analogs have been described in several U.S. patents, including U.S. Pat. Nos. 5,663,335, 6,150,539, 6,458,537, and 6,569,893, each of which is hereby incorporated by reference in its entirety. The compounds can be prepared, as described therein, from triptolide, a plant-derived diterpene triepoxide. Triptolide and its analogs have shown beneficial immunosuppressive and cytotoxic activity, as described, for example, in the above-referenced patents.

Exemplary triptolide analogs include 14-methyltriptolide (designated PG670; see US application pubn. no. 20040152767), triptolide 14-tert-butyl carbonate (designated PG695; see PCT Pubn. No WO 2003/101951), 14-deoxy-14α-fluoro triptolide (designated PG763; see U.S. Provisional Appn. Ser. No. 60/449,976), triptolide 14-(α-dimethylamino)acetate (designated PG702; see U.S. Pat. No. 5,663,335), 5-α-hydroxy triptolide (designated PG701; see U.S. Provisional Appn. Ser. No. 60/532,702), and 19-methyl triptolide (designated PG795; see U.S. Provisional Appn. Ser. No. 60/549,769). Each of these applications and publications is hereby incorporated by reference in its entirety.

Many of these compounds are believed to act as prodrugs, by converting in vivo to triptolide, as observed for PG490-88, above. Others, such as 14-deoxy-14α-fluoro triptolide, are not expected to undergo such conversion, but nonetheless exhibit biological activities shown by triptolide (e.g. cytotoxicity in human T cell lymphoma (Jurkat) cells and inhibition of IL-2), as reported in U.S. application Ser. No. 60/449,976, cited above.

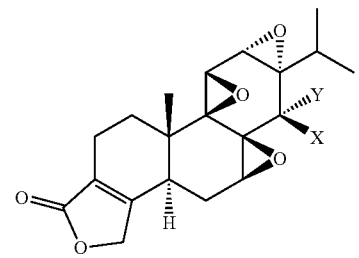

Exemplary Triptolide Derivatives and Prodrugs

|  | X | Y |
|---|---|---|
| PG490-88 | —O(CO)CH$_2$CH$_2$COOH | —H |
| PG670 | —OH | —CH$_3$ |
| PG695 | —O(CO)OC(CH$_3$)$_3$ | —H |
| PG702 | —O(CO)CH$_2$N(CH$_3$)$_2$ | —H |
| PG673 | —H | —F |

Triptolide analogs for use in screening, according to the methods described herein, are not limited to the compounds described or shown above.

Triptolide analogs for screening can be generated by combinatorial chemistry or other type of preparation to generate diversity of chemical structure or substituents. Alternatively, analogs can be designed to derive a structure with predicted binding capacity for a selected target molecule.

III. Screening of Triptolide Analogs

A. Methods

Various assays can be used to measure the interaction of a triptolide-related compound with one of the target proteins, and to compare the binding of, and affinity of, two or more triptolide-related compounds.

For those molecules with chaperone function, client molecules requiring this function for activity can be used in an assay for binding and functional inhibition (or functional alteration) of the target molecule chaperone function. For example, HSP90 β binds to serine/threonine kinase Akt/PKB, allowing it to be dephosphorylated by protein phosphatase 2A. Binding of Akt to HSP90 β can be detected in BALB/3T3 cells by doing an immunoblot analysis after precipitation of cell extracts with anti-Akt antibody. Binding to HSP90 β by a test compound and consequent inhibition of the interaction of HSP90 β with Akt is evidenced by a diminution in the result of the immunoblot analysis. (See e.g. Sato et al., 2000.)

A purified target protein preparation can be radioactively labeled with an isotope other than $^3$H. A triptolide-related compound can be incubated with an appropriate human cell type, such as Jurkat, and an extract made from the cells. The labeled purified target protein can then be mixed with the cell extract containing $^3$H-labeled triptolide-related compound, and the mixture subjected to purification designed to reveal the particular target protein. This approach should demonstrate co-purification of the two different labels, showing that the target protein co-purifies with the triptolide-related compound, demonstrating binding of the compound to the target molecule. Purified targets can be labeled with $^{32}$P, $^{33}$P, $^{14}$C, and $^{35}$S through post-translational modifications (e.g. phosphorylation using $^{32}$P or $^{33}$P) or translation of mRNA in systems containing labeled amino acids (e.g. protein synthesis using $^{14}$C or $^{35}$S).

Competitive binding can also be used to compare binding affinity of different triptolide-related compounds to specific triptolide target molecules. Triptolide-related compounds can be radioactively labeled with an isotope such as $^3$H. One of the labeled compounds can be incubated with either a purified target protein preparation or an appropriate cell type (such as Jurkat). In parallel, a similar incubation of labeled compound with target protein or cells is conducted in the presence of a second, unlabeled triptolide-related compound. Comparison of the radioactivity associated with the purified target protein, or the extracted and semi-purified target protein from the cell incubation, indicates whether the competing triptolide-related compound reduced the binding of the radiolabeled triptolide-related compound. A variety of comparisons like this can be made to determine how test compounds compete with one another for target protein binding. Higher affinity would be associated with increased binding of the competitor and decreased binding of the radiolabeled test compound.

Techniques such as surface plasmon resonance may also be used to measure the comparative affinities of binding of the triptolide-related compounds to purified target proteins.

Enzymatic activity can be used to assess the binding of triptolide-related molecules to target proteins that act as enzymes. Akt is a serine/threonine kinase, and a cellular assay with analysis of inhibition of the kinase activity of Akt resulting from binding of a triptolide-related compound can be used as an assay for such binding and can provide a means of comparing the binding affinities of various triptolide-related compounds. The reducing activity of thioredoxin reductase for thioredoxin-1 can provide an assay for the activity of the enzyme and therefore a means to determine the alteration in enzymatic activity induced by binding of a triptolide-related compound. Such an assay can then be used to compare the binding affinities of various triptolide-related compounds.

Similarly, the enzymatic activity of Phosphatidyl Inositol 3 Kinase can be assayed, as described, for example, by Yano et al. (1993). Modulation of the enzymatic activity by a triptolide-related compound can be assessed. The enzyme assay can also be used to compare the binding of various triptolide-related compounds.

Eukaryotic Translation Elongation Factor 2 kinase also has enzymatic activity that can be used to assess and compare the binding of various triptolide-related compounds. Treatment with insulin of quiescent Chinese hamster ovary cells expressing the human insulin receptor induces an increase in expression of Eukaryotic Translation Elongation Factor 2 kinase and increased phosphorylation of Eukaryotic Translation Elongation Factor 2 (Redpath et al., 1996). Addition of a triptolide-related compound to an assay based on this observation will reveal the modulatory effects upon the activity of Eukaryotic Translation Elongation Factor 2 kinase. This assay can also be used to compare the binding and activity of various triptolide-related compounds.

Human Serine/Threonine Protein Phosphatase 2A (130 KDa regulatory subunit PP2A) ) is one of the major serine/threonine-specific protein phosphatases. One of the signaling targets of Human Serine/Threonine Protein Phosphatase 2A is the mitogen-activated protein kinase (MAPK/ERK) cascade. The phosphatase activity of this target molecule can be used to assess the impact of a triptolide-related compound in a cell-based assay. Modulation of the downstream MAPK/ERK cascade can be used to compare the binding affinities of various triptolide-related compounds. Two alternative approaches involve regulation by Human Serine/Threonine Protein Phosphatase 2A of Ras signaling by dephosphorylating Kinase Suppressor of Ras (KSR) and Raf-1 on critical 14-3-3 binding sites. The modulation of binding of KSR and/or Raf-1 to 14-3-3 can be analyzed in a cell-based assay to reveal and compare the binding activities of triptolide-related compounds. Alternatively, alteration of the Human Serine/Threonine Protein Phosphatase 2A-mediated dephosphorylation of KSR or Raf-1 by a triptolide-related compound would be an indication of binding and activity of such compounds.

Human Serine/Threonine Protein Phosphatase 2A positively regulates Ras signaling by dephosphorylating Kinase Suppressor of Ras (KSR) and Raf-1 on critical 14-3-3 binding sites (Ory et al., 2003). Inhibition of PG789 would suppress the Ras activation pathway.

The activity of Protein Disulfide Isomerase can be assayed by measuring the ability to catalyze the refolding of reduced and denatured RNase (Lundstrom et al., 1992). During the process of RNase refolding, non-native as well as native disulfide bonds form; therefore, both disulfide oxidation as well as isomerization reactions must occur to achieve the native folded state. Alteration in the measured RNase activity in the assay of Protein Disulfide Isomerase indicates binding and modulating activity of triptolide-related compound(s).

B. Selection of Analogs for Treatment based on Target Molecule Bioproperties

Screening of triptolide analogs for binding to a target molecule, selected from those listed above, can be used to identify second-generation compounds with improved and/or selective binding. Enhanced binding to a target molecule may result in a lower dose for treatment and/or serve to increase the specificity of the treatment for a particular disease state.

For example, several of the triptolide target molecules express or regulate enzymatic (catalytic) activity. These include Thioredoxin Reductase (PG774), Protein Disulfide Isomerase (PG775), Phosphatidyl Inositol 3 Kinase (Class II) (PG776), Eukaryotic Translation Elongation Factor 2 (EEF2) (PG786) and Human Serine/Threonine Protein Phosphatase 2A (130 KDa regulatory subunit PP2A) (PG789). These target molecules can be used to assess the enzyme inhibitory activity of triptolide-related compounds. It is also possible that triptolide analogs may act as agonists of the activity of one or more of these triptolide target molecules that may function as enzymes. Modulation of enzyme activity could be used in compound screening as a surrogate for a more broadly function-driven cell-based assay such as induction of cytotoxicity in Jurkat cells or inhibition of IL-2 production by Jurkat cells.

As one example, 14-3-3 $\epsilon$ (PG773) and related proteins (i.e. other isotypes of 14-3-3) are abundant in the CNS, with the highest concentration found in the brain. The elevation of 14-3-3 $\epsilon$ in Alzheimer's disease and its deposition in Parkinson's disease suggest a contribution to the pathophysiology of these diseases. Inhibition of 14-3-3 $\epsilon$, e.g. by binding to a triptolide analog, may inhibit binding to client proteins and reduce deposition of insoluble protein complexes, possibly slowing the progression of these neurodegenerative diseases.

The anti-apoptotic function of PG773 may indicate that disease areas with less than optimal cell death, such as cancer, autoimmune disease and possibly organ transplantation, may also benefit from treatment with triptolide-related agents.

As a further example, thioredoxin reductase (PG774) is involved in cell growth stimulation and inhibition of apoptosis, and is pertinent to cancer and chronic autoimmune diseases such as rheumatoid arthritis. PG774 is increased in Alzheimer's disease, where is may contribute to oxidative stress and neurodegeneration.

Pannus cells in osteoarthritic cartilage are positive for vimentin (PG778) (Yuan et al., 2004). Use of a triptolide related compound, particularly one that strongly or selectively binds PG778, may therefore be effective in treatment of degenerative diseases such as osteoarthritis and rheumatoid arthritis.

Some of the identified triptolide target proteins have relevance to both anticancer and immunosuppressive activity. Phosphatidyl Inositol 3 Kinase (Class II) (PG776), and the family of proteins of which 14-3-3 $\epsilon$ (PG773) is a member, participate in signaling cascades by promoting and coordinating protein-protein interactions. In T lymphocytes, IL-2 signaling can diminish the expression of one of the chains of another interleukin through a Phosphatidyl Inositol 3 Kinase (Class II) (PG776)-dependent mechanism. Vimentin (PG778) expression is differentially regulated by IL-2 and IL-4; cells grown in IL-2 typically express much more Vimentin than those grown in IL-4, thereby demonstrating physiological relevance. Finally, a covalent association of Protein Disulfide Isomerase (PG775) with expressed human IL-2 has been reported.

C. Selective Binding; Reduction of Side Effects

Triptolide analogs can be screened for selective binding to one or more of the diverse group of target molecules identified herein. Analogs showing selective binding to one or more target molecules and reduced binding to other target molecules (particularly those involved in side effects or expressed in tissues or cells where toxicity is observed) are selected as likely to provide reduced side effects and an improved safety profile, allowing reduced dose levels while still retaining an adequate or desired degree of efficacy. Reduced dosing levels will contribute to a reduction in side effects by further reducing the effect upon target molecules associated with toxicity.

The distribution of the triptolide target molecules in cell types, tissues, organs, or organ systems can be correlated to either beneficial effects or side effects (toxicity) of triptolide and its analogs. For example, certain tissues or cells, such as the immune system and T lymphocytes, can be correlated to efficacy in the area of immunosuppression. Other tissues or cells, such as the testes, can be correlated to side effects, in view of the observed anti-spermatogenic activity of triptolide compounds.

For example, one of the group of hypothetical proteins identified as targets of triptolide (PG777, PG787, PG788 and PG790) may have a cell, tissue or organ distribution pattern that uniquely correlates to the side effects of triptolide (e.g., the testes). More particularly, vimentin (PG778), although expressed elsewhere, is used as a marker for immunohistochemical identification of Sertoli cells (Wang et al., 2002b). As a component of Intermediate filaments, it is involved in the compartmentation of the Sertoli cell into a perinuclear stable zone and a peripheral trafficking zone with fluctuating shape that is important with respect to the germ cell-supporting surface of the cell (Aumuller et al., 1992). Experimental reduction in intratesticular testosterone concentration in rats results in collapse of the Sertoli cell vimentin (PG778) cytoskeleton to a perinuclear localization and the apoptotic death of spermatocytes (Show et al., 2003). This observation on the importance of vimentin in the Sertoli cell support of germ cell development provides support for a mechanism of triptolide-induced anti-spermatogenic side effects. Accordingly, PG778 can be used in the screening of triptolide analogs for reduced binding to this particular target molecule, as a way of reducing this side effect.

A triptolide target molecule that is identified as a chaperone protein or a protein with a variety of client proteins, e.g. HSP 90β (PG771) or 14-3-3 $\epsilon$ (PG773), may interact with a protein for which unaltered function is necessary in a restricted cell, tissue or organ to avoid side effects. A triptolide analog may produce side effects only in this cell, tissue or organ, by affecting the chaperoning function of this target molecule and the manner in which it interacts with its client protein(s).

The correlation of the expression of the target molecules to the side effect observed in a particular tissue or organ can also provide information on the mechanism of the side effect. This information may suggest ways to ameliorate the side effect without compromising the efficacy of treatment with second-generation triptolide analogs.

D. Determination of whether a Disease State is Amenable to Treatment

The expression patterns of the triptolide target molecules can be used to determine whether a particular disease or disorder is amenable to treatment with triptolide-related compounds. Thus, target molecule expression that is quantitatively or qualitatively different in the cells, tissues, organs or fluids (including the blood stream, gastrointestinal tract and lymph) of individuals with a particular disease or disorder, compared to normal individuals, would suggest that the disease could be treated with triptolide analogs. Expression of the target molecules could also be used to identify additional disease states that could benefit from treatment with triptolide analogs.

In general, the level, state of activation, and/or cellular location of a triptolide target molecule, selected from the group listed above, in a cell or tissue sample in which the disease state is present, is compared with the respective level, state of activation, and/or cellular location of the triptolide target molecule in a normal cell or tissue sample. Such comparison typically entails separately determining the level, state of activation, and/or cellular location of the triptolide target molecule in the diseased cell or tissue sample and in the normal cell or tissue sample. Methods for determining these factors are known in the art, and include ELISA methods and antibody-based methods, as described generally in the Examples below. The information with respect to the normal sample may also be predetermined or previously known. The disease state is considered potentially amenable to treatment with triptolide or a triptolide analog if the level, state of activation, and cellular location of the triptolide target molecule differs between the diseased sample and the normal sample.

For example, the target molecule may be present at a higher level (e.g. more highly expressed) in a diseased sample than in a normal sample. Alternatively, or in addition, it may be present in a different state of activation; that is, it may be phosphorylated, acylated, or truncated. Alternatively, or in addition, its cellular localization (e.g. nuclear vs. cytoplasmic) may be altered.

Such an evaluation may be followed by administration of triptolide or a triptolide analog to the cell or tissue sample in which the disease state is present, and in which an altered level, form, and/or localization of a triptolide target molecule is observed. Preferably, the analog is one that shows enhanced and/or selective binding to the target molecule. Comparison of the pattern of expression (i.e. level, state of activation, and/or cellular location) of the target molecule in the diseased tissue and in normal tissue can then be repeated, thereby determining if the triptolide or triptolide analog is potentially effective to modulate or alleviate the disease state, by influencing the activity of the target molecule. Such comparison is, in general, useful for determining the status of the disease, e.g. to evaluate whether an ongoing treatment is effective, if the intensity of treatment should be altered (reduced or increased), or if treatment should be altered to achieve better results.

Treatment of a disease state with triptolide-related molecules is preferably indicated when the target molecules are not highly expressed in the areas where toxic side effects are manifested. The cell, tissue and/or organ distribution of expression of the triptolide target molecules may thus be used to determine a safer course of treatment, avoiding toxic side effects while still achieving efficacy.

Expression of the target molecules can also be assessed to identify additional disease states that would benefit from treatment with triptolide analogs. Atypical expression of the target molecule in a cell type or tissue compartment where it is not found in normal patients would suggest involvement in a disease process, and may even provide an explanation of the disease process or constitute a marker of disease state. Enhanced expression of a target molecule would indicate the possibility that triptolide analogs could be used to advantage in treating this particular disease. For example, expression of L-plastin (PG772) has been identified as a potential marker for metastatic colon carcinoma (Otsuka et al., 2001).

Correlation of patient genotype with expression profiling of triptolide target molecules can also be used to make treatment decisions regarding triptolide analogs. Patients can be genotyped (e.g. using genetic markers such as single nucleotide polymorphisms, SNPs) and profiled using expression assays to determine expression of one or more of the triptolide targets. The correlation of the genotypic marker(s) with the target expression profile(s), and the degree or specificity of binding of triptolide analog(s) to the target molecule(s), can be used to select a triptolide analog for treatment to achieve efficacy and/or avoid toxicity.

This approach will depend upon a direct relationship between a genotypic marker and a target of triptolide, as well as diversity in the expression of target molecules (present or absent, or expressed at a range of levels), activity of target molecules, or activity of pathways involving target molecules. The differences observed between individuals in these areas will indicate the range of target-related expression. The particular target molecule or pathway expression will provide information as to the desirability of treatment with a triptolide-related molecule.

E. Combination Therapy

The molecular target(s) of triptolide disclosed herein can also be used to select appropriate drugs or agents for combination therapy in a given indication; i.e. compounds that can be used in combination with a triptolide-related compound to produce enhanced efficacy with reduced or acceptable side effects. The drug or agent added to the treatment regimen of the triptolide-related compound can be administered at a dose level, route, or schedule that is the same as or different from that of the triptolide-related compound.

In one aspect, the identities and properties of the target molecules of triptolide disclosed herein are compared to similar information describing the target molecules of drugs commonly used in the treatment of a particular disease state. Knowledge of the target molecules and their cellular pathways can suggest agents that would be anticipated to be additive in terms of therapeutic efficacy, or to interact in a positive or a negative manner, when used in combination.

A triptolide analog can be selected for use in combination therapy with a drug that binds to a target molecule to which the triptolide analog binds preferentially, or to a molecule that is in the same cellular signaling pathway as that target molecule. In this manner, both agents are intended to act upon the same mechanistic pathway. As an example, geldanamycin, an antitumor antibiotic, is known to bind to the triptolide target molecule HSP 90β. Accordingly, a triptolide compound known to bind preferentially to this target could be selected for use in combination therapy with this drug. Other examples of this strategy, pertaining to other selected triptolide target molecules, include the following:

14-3-3 ε: Human DNA topoisomerase II α (topo II), a ubiquitous nuclear enzyme, is essential for normal and neoplastic cellular proliferation and survival. Several common anticancer drugs exert their cytotoxic effects through interaction with topo II. 14-3-3 ε is a topo II-interacting protein that negatively affects the ability of the chemotherapeutic agent etoposide to trap topo II in cleavable complexes with DNA, thereby preventing DNA strand breaks (Kurz et al., 2000). This effect appears to be due to reduced DNA binding activity. Binding of triptolide-related compounds to 14-3-3 ε may interfere with the interaction of this molecule with topo II, thereby allowing it to trap topo II in cleavable complexes with DNA and causing DNA strand breaks. This would enhance the activity of antineoplastic agents that act by binding to and trapping topo II.

Phosphatidyl Inositol 3 Kinase: TNF-related apoptosis-inducing ligand (TRAIL) very efficiently promotes apoptosis of primary human melanocytes. Stem cell factor (SCF), a physiologic melanocyte growth factor that activates both the phosphatidyl-inositol-3 kinase (PI3K) and the extracellular regulated kinase (ERK) pathways, strongly protects melanocytes from TRAIL and staurosporine killing (Larribere et al., 2004), and could explain the mechanism by which melanomas acquire their resistance to apoptosis. Inhibition of PI3K or its downstream target Akt completely blocks the antiapoptotic effect of SCF. Only a sustained PI3K activity can protect melanocytes from apoptosis, thereby indicating that the PI3K/AKT pathway plays a pivotal role in melanocyte survival. Inhibition of PI3K by a triptolide derivative may therefore enhance the activity of TRAIL or staurosporine in melanoma by blocking the antiapoptotic effect of SCF. A triptolide-related compound may therefore be used in combination with TRAIL, staurosporine, or proteins or compounds that exert similar activities or are related to these agents (e.g., TNF is related to TRAIL).

As a further example, the PI-3 kinase pathway may be critical for survival and proliferation of myelofibrosis with myeloid metaplasia (MMM) progenitor colonies (Mesa et al., 2003). MMM progenitor colonies are highly sensitive to PI-3 kinase inhibitor LY294002. This approach is used to treat other hematologic malignancies. Triptolide derivatives may enhance the activity of agents like PI-3 kinase inhibitor LY294002 by inhibiting the same target. Furthermore, triptolide derivatives could be used with farnesyl transferase inhibitors such as R115777.

Akt and phosphatidyl inositol 3-kinase: VEGF (vascular endothelial growth factor) stimulates rapid and sustained phosphorylation of Akt/PKB that is inhibited by the phosphatidyl inositol 3-kinase (PI3-K) kinase inhibitor wortmannin (List et al., 2004). Preincubation with wortmannin inhibits VEGF-induced colony formation in a concentration-dependent fashion. The rHu-VEGF-induced clonogenic response and Akt phosphorylation is abolished by the VEGF-RTK inhibitor SU-5416. VEGF interaction with either VEGFR-1 or VEGFR-2 initiates a clonogenic response in AML cells that is PI3-kinase dependent. A triptolide derivative could be used in combination with an inhibitor of VEGF or an inhibitor of a VEGF receptor (like SU-5416 or another drug with similar activity) or another PI3K kinase inhibitor (like wortmannin or another drug with similar activity) to enhance the inhibition of the growth of cancer cells in patients with myeloid malignancies (e.g., myeloblasts in AML).

L-plastin: Triptolide-related compounds can also be used in combination with agents that block the action of agents that induce one of the triptolide targets. L-Plastin, one of the triptolide targets, is normally a leukocyte-specific actin-binding protein. L-plastin gene expression is positively regulated by testosterone in androgen receptor (AR)-positive prostate and breast cancer cells (Lin et al., 2000). The L-plastin gene is therefore inducible by testosterone. L-plastin contributes to invasiveness of prostate cancer cells. Interaction with the triptolide target, L-plastin, by a triptolide-related compound may enhance the activity against prostate tumors treated with anti-androgen therapy (to block testosterone effects, one of which is L-plastin induction). Therefore, triptolide-related compounds could be used in combination with anti-androgen therapy. L-plastin is also induced by hormonal stimulation in breast cancer; accordingly, triptolide-related compounds can be used in combination with anti-androgen or anti-estrogenic therapy.

The above examples employ the strategy of combination therapy using agents that affect the same cellular pathway. Alternatively, a triptolide-related compound having a particular target specificity can be combined with another therapeutic agent that affects different cellular pathway(s) related to efficacy in treating a particular disease state. Such a combination would be likely to be at least additive, and possibly synergistic, in therapeutic activity. Such a combination would be likely to produce enhanced efficacy, perhaps at a lower dose of each agent, while reducing dose-related side effects of the treatment. This will allow the potential convergence of toxic side effects to be avoided and combination treatments selected to enhance efficacy.

IV. Therapeutic Indications for Treatment with Triptolide Related Compounds

The following disease states have been shown to be amenable to treatment with triptolide and its prodrugs and other analogs. Such disease states would be preferred target areas for treatment with second-generation triptolide analogs identified by screening for binding to the triptolide target molecules identified herein. The compounds may be used in combination with conventional therapeutic agents, e.g. those identified as described in Section III.E above.

A. Cancer

As used herein, "cancer" refers to all types of cancer or neoplasm or malignant tumors found in mammals especially humans, including leukemias, sarcomas, carcinomas and melanoma. The term "leukemia" refers broadly to progressive, malignant diseases of the blood-forming organs and is generally characterized by a distorted proliferation and development of leukocytes and their precursors in the blood and bone marrow. The term "sarcoma" generally refers to a tumor that is made up of a substance like the embryonic connective tissue and is generally composed of closely packed cells embedded in a fibrillar or homogeneous substance. The term "melanoma" is taken to mean a tumor arising from the melanocytic system of the skin and other organs. The term "carcinoma" refers to a malignant new growth made up of epithelial cells tending to infiltrate the surrounding tissues and give rise to metastases.

Included, for example, are cancers involving cells derived from reproductive tissue (such as Sertoli cells, germ cells, developing or more mature spermatogonia, spermatids or spermatocytes and nurse cells, germ cells and other cells of the ovary), the lymphoid or immune systems (such as Hodgkin's disease and non-Hodgkin's lymphomas), the hematopoietic system, and epithelium (such as skin, including malignant melanoma, and gastrointestinal tract), solid organs, the nervous system, e.g. glioma (Zhou et al., 2002), and musculoskeletal tissue. Cancer cell types include brain, including medulloblastoma, head and neck, breast, colon, small cell lung, large cell lung, thyroid, testicle, bladder, prostate, liver, kidney, pancreatic, esophageal, stomach, ovarian, cervical or lymphoma tumors. Treatment of breast, colon, lung, and prostate tumors is particularly contemplated. Treatment is targeted to slowing the growth of tumors, preventing tumor growth, inducing partial regression of tumors, and inducing complete regression of tumors, to the point of complete disappearance, as well as preventing the outgrowth of metastases derived from solid tumors.

Antitumor activity in vivo of a particular composition can be evaluated by the use of established animal models, as described, for example, in Fidler et al., U.S. Pat. No. 6,620,843. Clinical doses and regimens are determined in accordance with methods known to clinicians, based on factors such as severity of disease and overall condition of the patient.

B. Immune-mediated Diseases

Triptolide-related compounds are useful as immunosuppressive agents, e.g. as an adjunct to transplant procedures or in treatment of autoimmune disease. Included are human diseases of the immune system attributed to regulatory abnormalities. Immunoregulatory abnormalities have been shown to exist in a wide variety of "autoimmune" and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, psoriasis, pemphigus, Grave's disease and asthma. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow transplant or other transplant of hematopoietic stem cells from a donor tissue source containing mature lymphocytes, the transferred lymphocytes recognize the host tissue antigens as foreign. These cells become activated and mount an attack upon the host (a graft-versus-host response) that can be life threatening. Moreover, following an organ transplant, the host lymphocytes recognize the foreign tissue antigens of the organ graft and mount cellular and antibody-mediated immune responses (a host-versus-graft response) that lead to graft damage and rejection.

One result of an autoimmune or a rejection process is tissue destruction caused by inflammatory cells and the mediators they release. Anti-inflammatory agents such as NSAIDs act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Triptolide-related compounds have proven effective in immunosuppression therapy, as in treating an autoimmune disease, preventing transplantation rejection, or treating or preventing graft-versus-host disease (GVHD). See, for example, co-owned U.S. Pat. No. 6,150,539, which is incorporated herein by reference. They are also useful for treatment of other inflammatory conditions, such as traumatic inflammation, and in reducing male fertility.

Other uses include inhibiting rejection of a solid organ transplant, tissue graft, or cellular transplant from an incompatible human donor, thus prolonging survival and function of the transplant, and survival of the recipient. This use would include, but not be limited to, solid organ transplants (such as heart, kidney and liver), tissue grafts (such as skin, intestine, pancreas, gonad, bone, and cartilage), and cellular transplants (such as cells from pancreas, brain and nervous tissue, muscle, skin, bone, cartilage and liver).

Also included is inhibition of xenograft (interspecies) rejection; i.e. in preventing the rejection of a solid organ transplant, tissue graft, or cellular transplant from a non-human animal, whether natural in constitution or bioengineered, as well as treatment of autoimmune diseases or diseases having autoimmune manifestations, such as Addison's disease, autoimmune hemolytic anemia, autoimmune thyroiditis, Crohn's disease, diabetes (Type I), Graves' disease, Guillain-Barre syndrome, systemic lupus erythematosis (SLE), lupus nephritis, multiple sclerosis, myasthenia gravis, psoriasis, primary biliary cirrhosis, rheumatoid arthritis and uveitis, asthma, atherosclerosis, Hashimoto's thyroiditis, allergic encephalomyelitis, glomerulonephritis, and various allergies.

Further uses include the treatment and prophylaxis of inflammatory and hyperproliferative skin diseases and cutaneous manifestations of immunologically mediated illnesses, such as psoriasis, atopic dermatitis, pemphigus, urticaria, cutaneous eosinophilias, acne, and alopecia areata; various eye diseases such as conjunctivitis, uveitis, keratitis, and sarcoidosis; inflammation of mucous and blood vessels such as gastric ulcers, vascular damage caused by ischemic diseases and thrombosis, ischemic bowel diseases, inflammatory bowel diseases, and necrotizing enterocolitis; intestinal inflammations/allergies such as Coeliac diseases and ulcerative colitis; renal diseases such as interstitial nephritis, Good-pasture's syndrome, hemolytic-uremic syndrome and diabetic nephropathy; hematopoietic diseases such as idiopathic thrombocytopenia purpura and autoimmune hemolytic anemia; skin diseases such as dermatomyositis and cutaneous T cell lymphoma; circulatory diseases such as arteriosclerosis and atherosclerosis; renal diseases such as ischemic acute renal insufficiency and chronic renal insufficiency; and Behcet's disease.

Other indications related to immunosuppression include the treatment of inflammatory conditions such as asthma, both intrinsic and extrinsic manifestations, for example, bronchial asthma, allergic asthma, intrinsic asthma, extrinsic asthma and dust asthma, particularly chronic or inveterate asthma (for example, late asthma and airway hyperresponsiveness), as well as other inflammatory conditions, including traumatic inflammation, inflammation in Lyme disease, chronic bronchitis (chronic infective lung disease), chronic sinusitis, sepsis associated acute respiratory distress syndrome, and pulmonary sarcoidosis.

Immunosuppressive activity of compounds in vivo can be evaluated by the use of established animal models known in the art, as described, for example, in U.S. Pat. No. 6,150,539, which is incorporated herein by reference.

C. Organ Fibrosis

Triptolide-related compounds may also be used in the treatment of organ fibrosis, including certain lung diseases. Idiopathic pulmonary fibrosis (PF) is a progressive interstitial lung disease with no known etiology. PF is characterized by excessive deposition of intracellular matrix and collagen in the lung interstitium and gradual replacement of the alveoli by scar tissue as a result of inflammation and fibrosis. As the disease progresses, the increase in scar tissue interferes with the ability to transfer oxygen from the lungs to the bloodstream. A 14-succinimide ester of triptolide has been reported to block bleomycin-induced PF (G. Krishna et al., 2001). Accordingly, the compounds of the present invention may be useful for treatment of PF (see Intl. Appn. No. PCT/US04/20347). Treatment of other respiratory diseases, such as sarcoidosis, fibroid lung, and idiopathic interstitial pneumonia is also considered, as is the treatment of particular TGF-β associated inflammatory disorders, including obliterative airway disease, renal fibrosis, diabetic nephropathy, and liver fibrosis (see U.S. Provisional Appn. Ser. No. 60/583,295).

Other diseases involving the lung and envisioned to be treatable by triptolide-related compounds include Severe Acute Respiratory Syndrome (SARS) and acute respiratory distress syndrome (ARDS). In particular, with respect to SARS, the reduction of virus content (SARS-CoV) before the peak of the disease process and the usefulness of corticosteroid treatment, as noted below, suggest that the development of the most severe, life-threatening effects of SARS may result from the exaggerated response of the body to the infection (immune hyperactivity) rather than effects of the virus itself (See also co-owned U.S. Provisional Appn. Ser. No. 60/483,335 and Intl. Appn. No. PCT/US04/20447, which are incorporated herein by reference.) Corticosteroid treatment has been used in SARS patients to suppress the massive release of cytokines that may characterize the immune hyperactive phase, in the hope that it will stop the progression of pulmonary disease in the next phase. Corticosteroid treatment has produced good clinical results in reduction of some of the major symptoms of SARS. However, there are several treatment-related side effects, and there is a clear need for more selective immunosuppressive and/or antiinflammatory agents.

D. CNS Diseases

Triptolide-related compounds may also be used in the treatment of certain CNS diseases. Glutamate fulfills numerous physiological functions, including an important role in the pathophysiology of various neurological and psychiatric diseases. Glutamate excitotoxicity and neurotoxicity have been implicated in hypoxia, ischemia and trauma, as well as in chronic neurodegenerative or neurometabolic diseases, Alzheimer's disease (AD), Huntington's disease and Parkinson's disease. In view of the reported neuroprotective effects of triptolide, particularly protection from glutamate-induced cell death (He et al., 2003; Wang et al., 2002a), compounds of the invention are envisioned to antagonize the neurotoxic action of glutamates and thus may be a novel therapy for such diseases.

Cerebral amyloid angiopathy is one of the pathological features of AD, and PC12 cells are extremely sensitive to induction of neurotoxicity by mutant β-amyloid protein aggregates. PC12 cells treated with β-amyloid exhibit increased accumulation of intracellular ROS and undergo apoptotic death (Gu et al., 2004). Beta-amyloid treatment induces NF-κB activation in PC12 cells, and increases the intracellular $Ca^{2+}$ level. Triptolide has been shown to markedly inhibit β-amyloid-induced apoptosis to inhibit the increase of intracellular $Ca^{2+}$ concentration induced by β-amyloid. Accordingly, triptolide-related compounds may be effective to prevent the apoptosis cascade induced by β-amyloid and preserve neuronal survival in AD patients.

Triptolide exerts a powerful inhibitory influence over lipopolysaccharide (LPS)-activated microglial activity by reducing nitrite accumulation, TNF-α and IL-1β release, and induction of mRNA expression of these inflammatory factors (Zhou et al., 2003). Triptolide also attenuates the LPS-induced decrease in $^3$H-dopamine uptake and loss of tyrosine hydroxylase-positive neurons in primary mesencephalic neuron/glia mixed culture (Li et al., 2004). Triptolide appeared to exert a neurotrophic effect without LPS. Triptolide also blocked LPS-induced activation of microglia and excessive production of TNF-α and nitrite. Triptolide may protect dopaminergic neurons from LPS-induced injury by inhibiting microglia activation, which is relevant to Parkinson's disease, further illustrating the neuroprotective potential of triptolide-related compounds.

Tripchlorolide, which has been shown to be a prodrug of triptolide, promotes dopaminergic neuron axonal elongation in primary cultured rat mesencephalic neurons and protects dopaminergic neurons from a neurotoxic lesion induced by 1-methyl-4-phenylpyridinium ion (Li et al., 2003). Tripchlorolide stimulates brain-derived neurotrophic factor mRNA expression as revealed by in situ hybridization. Furthermore, in an in vivo rat model of PD in which FK506 shows neurotrophic activity, administration of tripchlorolide at 0.5-1 μg/kg improves recovery of rats undergoing neurosurgery, produces significant sparing of SN neurons and preservation of the dendritic processes surrounding tyrosine hydroxylase positive neurons, attenuates dopamine depletion, increases the survival of dopaminergic neurons and attenuates the elevation of TNF-α and IL-2 levels in the brain (Cheng et al., 2002). Moreover, tripchlorolide demonstrates neurotrophic activity at a concentration lower than needed for neuroprotective and immunosuppressive activity.

Recent evidence from MS patients in relapse suggests an altered glutamate homeostasis in the brain. Neurotoxic events occurring in MS patients can be responsible for oligodendrocyte and neuronal cell death. Antagonizing glutamate receptor-mediated excitotoxicity by treatment with triptolide-related compounds may have therapeutic implications in MS patients. Other CNS diseases such as Guillain-Barre syndrome, Meniere's disease, polyneuritis, multiple neuritis, mononeuritis and radiculopathy may also be treated with triptolide-related compounds.

Materials and Methods

General Procedure: Identification of Triptolide Target Molecules

Triptolide target molecules were isolated and identified by purification and identification of molecules that bind $^3$H-triptolide. Jurkat cells from expanding cultures were labeled with $^3$H-triptolide by cultivation at 37° C. with 5% $CO_2$ for a period of time between a few hours and overnight (usually 6-7 hours) and harvested by centrifugation and washing in ice-cold phosphate buffered saline. The cells (usually $1-3 \times 10^6$/ml) were generally labeled with $^3$H-triptolide to a final concentration of 35 nM (100 μCi/200 ml of medium). Collected cell pellets were pooled, and the cells were either extracted and subjected to separation and purification at that time, or were frozen and stored at −20° C. as pellets for extraction and investigation at a later time.

The cells were extracted with M-per buffer (Pierce) and homogenized in presence of a protease inhibitor cocktail, sometimes including other reagents such as deoxyribonuclease (DNase). The extracts were purified and separated and the components identified by standard techniques, including preparative and analytical FPLC fractionation, anion exchange, cation exchange, and hydrophobic interaction and sodium dodecyl sulfate (SDS) polyacrylamide gel electrophoresis (PAGE). When the extracts components were found not to be sufficiently purified, enriched or reduced in number, 2D gel electrophoresis was employed, followed by fluorography for $^3$H-associated radioactivity detection, and MALDI/MS of the corresponding peptides (after proteolysis) and peptide fingerprinting. (Peptide fingerprinting uses the peptide masses obtained by enzymatic digestion to search protein and DNA databases for proteins that show a similar theoretical digest pattern; see e.g. Shevchenko et al., 1996a and b). Otherwise, the 2D gel electrophoresis and fluorography step was bypassed, and MALDI/MS after proteolysis was used.

Specific examples of target molecule identification are provided in Examples 1-6 below.

General Procedures: Quantification of Target Molecules

The target molecules can be detected in a cell or tissue sample using, for example, an enzyme-linked immunosorbent assay (ELISA) or, for the target proteins for which there are antibodies available (such as PG771-776, PG778, and PG789), a fluorochrome-based quantitation system.

One of the most useful approaches to determine the target protein concentration in a sample is the two-antibody sandwich ELISA. If a purified target protein standard is available, the assay can determine the absolute amounts of target protein in a sample. The sandwich ELISA requires two antibodies that bind to epitopes that do not overlap on the target molecule. This can be accomplished with either two monoclonal antibodies that recognize discrete sites or one batch of affinity-purified polyclonal antibodies.

In carrying out this assay, one antibody (the capture antibody) is purified and bound to a solid phase. The sample to be assayed for target protein content is then added and allowed to complex with the bound antibody. Unbound products are removed by washing, and a labeled second antibody (the detection antibody) is allowed to bind to the antigen, thus completing the sandwich. The assay is then quantitated by measuring the amount of labeled second antibody bound to the matrix, often through the use of a colorimetric substrate. Enzymes can be used that convert a colorless substrate to a colored product (e.g., p-nitrophenylphosphate is converted to the yellow p-nitrophenol by alkaline phosphatase). Substrates used with peroxidase include 2,2'-azo-bis(3-ethyl benzthiazoline-6-sulfonic acid), o-phenylenediamine and 3,3',5,5'-tetramethyl benzidine base, which yield green, orange, and blue colors, respectively. In addition to enzymes, antibodies can be labeled with radioactive atoms (such as an appropriate isotope of iodine) or biotin. With a biotin-labeled second antibody, advantage is taken of the strong affinity of avidin or streptavidin for biotin, and fluorochrome or enzyme-labeled avidin or streptavidin is used for detection.

EXAMPLE 1

Isolation and Identification of PG771, PG772 and PG773

These target molecules were identified via FPLC fractionation of $^3$H-PG490-incubated Jurkat cells, followed by 2D gel electrophoresis, radioautography (fluorography following gel treatment with radiation-sensitive ENHANCE), MALDI/MS, and protein identification. $^3$H-PG490-labeled Jurkat cell extract ($3.2 \times 10^9$ cells) was loaded on to a Hydrophobic Interaction Chromatography (HIC) column. $^3$H-associated HIC-bound proteins were eluted in four different fractions. Radioactive peaks 2 and 3 were individually desalted and loaded on to a MONO Q anion exchange column. $^3$H-associated bound proteins were eluted and further fractionated on Gel Filtration chromatography. Fraction #4 (from HIC peak 3) and Fraction #9 (from HIC peak 2) of Gel Filtration were analyzed by MALDI-MS and peptide fingerprinting.

MALDI-MS peptide fingerprinting analysis identified HSP 90β (PG771) in fraction #4 and L-plastin (PG772) in fraction #9. A 2D-gel electrophoresis of fraction #4 identified multiple spots on the chromatogram. To identify the protein with the $^3$H-associated counts, gels were treated with ENHANCE (NEN), washed with dH$_2$O, dried and fluorographed. A positive spot on the film (fluorographically positive, therefore positive for $^3$H-associated radioactivity) was seen near the 29 kDa protein marker. This spot was subsequently identified as 14-3-3 ε (PG773) based on the highest probability in MALDI-MS peptide fingerprinting analysis. L-plastin (PG772) was also identified as described in Example 2.

HSP 90β (PG771) was also identified following a combination of separation procedures similar to that described below for PG786, PG787 and PG788, including PAGE, Gel Filtration, 2-D gel electrophoresis, fluorography and MALDI/MS. PG771 was identified based on the highest probability in the MALDI/MS peptide fingerprinting analysis.

EXAMPLE 2

Isolation and Identification of PG772, PG774 and PG775

Thioredoxin Reductase (PG774) and Protein Disulfide Isomerase (PG775) were identified via FPLC fractionation of $^3$H-PG490-incubated Jurkat cells, followed by 2D gel electrophoresis, fluorography after gel treatment with radiation-sensitive ENHANCE, MALDI/MS and protein identification. $^3$H-PG490-labeled Jurkat cell extract was loaded on to a Prep Q anion exchange column. $^3$H-associated Prep Q-bound proteins were eluted in several fractions that were combined into two pools. The pooled material was desalted, and the two pools were individually loaded onto a Mono Q anion exchange column. The bound material was eluted, and the fractions containing radioactivity (#43) were further fractionated on Gel Filtration chromatography. From Mono Q-bound fraction #43, gel filtration fractions #17 and #18 were pooled and subjected to 1D PAGE. After treatment with ENHANCE and fluorography to identify 3H-associated material in the gel, a single band was visible. This radioactive band was carefully excised and subjected to MALD/MS after proteolysis. Thioredoxin Reductase (PG774) was initially identified by MALDI-MS peptide fingerprinting analysis. After eliminating from consideration the MALDI/MS peptide signals for Thioredoxin Reductase, L-plastin (PG772) was identified in a second peptide fingerprinting analysis of the MALDI-MS data. After eliminating from consideration the MALDI/MS peptide signals for L-plastin, Protein Disulfide Isomerase (PG775) was identified in a third peptide fingerprinting analysis of the MALDI-MS data.

EXAMPLE 3

Isolation and Identification of PG776

$^3$H-triptolide-labeled Jurkat cell extract was loaded on to a Prep Q anion exchange column. $^3$H-associated Prep Q-unbound proteins were loaded on to a Hydrophobic Interaction Chromatography (HIC) column. $^3$H-associated HIC-bound proteins were eluted in four different fractions. The radioactive peaks were desalted, and one of the pools was loaded onto a Mono Q anion exchange column. The bound material was eluted, and one of the fractions containing radioactivity (#38) was further fractionated on Gel Filtration chromatography. Fractions #8 and #9 of Gel Filtration were pooled and subjected to proteolysis and MALD/MS, resulting in identification of Phosphatidyl Inositol 3 Kinase—Class II (PG776) by peptide fingerprinting analysis.

EXAMPLE 4

Isolation and Identification of PG777

$^3$H-triptolide-labeled Jurkat cell extract was loaded on to a Prep Q anion exchange column. $^3$H-associated Prep Q-unbound proteins were loaded on to a Hydrophobic Interaction Chromatography (HIC) column. $^3$H-associated HIC-bound proteins were eluted, pooled in 2 groups containing the radioactive peaks, and desalted. The pool of fractions 43-49 (HIC bound) was loaded onto a Mono Q anion exchange column. The bound material was eluted, two of the fractions containing radioactivity were pooled (#30 and #31), and the Mono Q pool was further fractionated on Gel Filtration chromatography. Fractions #19 and #20 of Gel Filtration were pooled and subjected to proteolysis and MALD/MS, resulting in identification of hypothetical protein FLJ20297 (previously designated FLJ29756) from a cDNA library by peptide fingerprinting analysis (PG777).

EXAMPLE 5

Isolation and Identification of PG778

$^3$H-triptolide-labeled Jurkat cell extract was loaded on to a Prep Q anion exchange column. $^3$H-associated Prep Q-unbound proteins were loaded on to a Hydrophobic Interaction Chromatography (HIC) column. $^3$H-associated HIC-bound proteins were eluted in four different fractions. The radioactive peaks were desalted and one of the pools was loaded onto a Mono Q anion exchange column. The bound material was eluted, two of the fractions containing radioactivity were pooled (#32 and #33), and the Mono Q pool was further fractionated on Gel Filtration chromatography. Fraction #12 of Gel Filtration was subjected to proteolysis and MALD/MS, resulting in identification of Vimentin (PG778) by peptide fingerprinting analysis.

EXAMPLE 6

Isolation and Identification of PG786, PG787, PG788, PG789 and PG790

$^3$H-triptolide-labeled Jurkat cell extract from 2×10$^9$ cells was treated with DNase and loaded onto PAGE tube gels. After electrophoresis, the gels were sliced, and the slices identified as 90-120 kDa and >120 kDa (using a parallel molecular weight marker gel) were electroeluted. The two electroeluted fractions were separated by S-200 Gel Filtration, the fractions containing the $^3$H-associated counts were separated by 2-D gel electrophoresis, and the spots containing $^3$H-associated proteins were revealed by fluorography after ENHANCE treatment. The spots were excised, subjected to trypsin digestion, and subjected to MALDI-MS and peptide fingerprinting analysis. Eukaryotic Translation Elongation Factor 2 (EEF2) (PG786) was identified based on the highest probability in the MALDI/MS peptide fingerprinting analysis.

PG788 was identified using a similar procedure. $^3$H-triptolide-labeled Jurkat cell extract from 2×10$^9$ cells was treated with DNase and loaded onto a Prep Cell PAGE apparatus rather than a series of individual PAGE tube gels. After electrophoresis, the Prep Cell was eluted with buffer, samples of the fractions were evaluated for $^3$H-associated counts, and the fractions constituting the peaks of $^3$H-associated counts were collected into four pools. These pools were individually separated by S-200 Gel Filtration, each pool yielding one major peak of $^3$H-associated counts. The fractions containing the $^3$H-associated counts were pooled and separated by 2-D gel electrophoresis, and the spots containing $^3$H-associated proteins were revealed by fluorography after ENHANCE treatment. The spots were excised, subjected to trypsin digestion and subjected to MALDI-MS and peptide fingerprinting analysis. Hypothetical Protein (GI 11277141), superfamily HSP 90 (PG788) was identified based on the highest probability in the MALDI-MS peptide fingerprinting analysis.

PG787 was identified following a combination of separation procedures similar to that used for PG786 and PG788, including PAGE, Gel Filtration, 2-D gel electrophoresis, fluorography, MALDI/MS and peptide fingerprinting analysis. PG787 Hypothetical Protein (GI 14758649), similar to heat shock protein (90 kDa) beta (PG787), was identified based on the highest probability in the MALDI/MS peptide fingerprinting analysis.

PG789 was identified following a similar combination of procedures. $^3$H-triptolide-labeled Jurkat cell extract was treated with DNase and loaded onto a Prep Cell PAGE apparatus. After electrophoresis, the Prep Cell was eluted with buffer, samples of the fractions were evaluated for $^3$H-associated counts, and the fractions constituting the peaks of $^3$H-associated counts were collected into four pools. The pool in the projected size range of approximately 90-120 kDa was separated by S-200 Gel Filtration, yielding one major peak of $^3$H-associated counts. The fractions containing the $^3$H-associated counts were pooled and subjected to 2-D gel electrophoresis, using a non-equilibrium pH gradient in the first (isoelectric focusing) dimension. The spots containing $^3$H-associated proteins were revealed by fluorography after ENHANCE treatment. The spot containing $^3$H-associated proteins (which had moved very little in the first dimension) was excised, subjected to trypsin digestion and subjected to MALDI-MS and peptide fingerprinting analysis. Human Serine/Threonine Protein Phosphatase 2A −130 KDa regulatory subunit, PP2A (PG789) was identified based on the highest probability in the MALDI-MS peptide fingerprinting analysis.

The triptolide target Hypothetical Protein—GI 7705346 (PG790) was identified by a combination of procedures similar to those described for the other targets.

It is claimed:

1. A method of screening triptolide or a triptolide analog selected from the group consisting of 2-hydroxytriptolide, 16-hydroxytriptolide (tripdiolide), 14-methyltriptolide, triptolide 14-tert-butyl carbonate, 14-deoxy-14α-fluoro triptolide, triptolide 14-(α-dimethylamino)acetate, triptolide 14-succinate, triptolide 14-γ-benzyl-N-benzyloxycarbonyl-(L)-glutamate ester, triptolide 14-N-t-butoxycarbonyl-α-t-butyl-L-glutamate ester, triptolide 14-β-benzyl-N-benzyloxycarbonyl-(L)-aspartate triptolide ester, triptolide 14-α-benzyl-N-benzyloxycarbonyl-D-glutamate ester, 14-isoglutamyl ester, 14-ethyl carbamate, 14-phenyl carbamate, 14-dimethylaminoethyl carbamate, N-methylpiperazinecarbonyl (carbamate), 14-ethyl carbonate, 14-phenyl carbonate, 14-ethoxyethyl carbonate, 14-methoxycarbonylmethyl carbonate, 14-(R)-α-methyl-tert-butoxycarbonylmethyl carbonate, 14-dimethylaminoethyl carbonate, 14-hydroxycarbonylmethyl carbonate, 5-α-hydroxy triptolide, 19-methyl triptolide, 18-deoxo-19-dehydro-18-benzoyloxy-19-benzoyl triptolide, 12-tosloxy-13-hydroxy triptolide and 18-glutaryl furanoid triptolide for binding to a triptolide target molecule and subsequent selection for further testing of its ability to influence activity of the target molecule, comprising:

(a) identifying a binding interaction between the tripolide analog and a triptolide target molecule selected from the group consisting of:

HSP 90 β (designated PG771),
L-plastin (designated PG772),
14-3-3 ε (designated PG773),
Thioredoxin Reductase (designated PG774),
Protein Disulfide Isomerase (designated PG775),
Phosphatidyl Inositol 3 Kinase (Class II) (designated PG776),
Hypothetical Protein FLJ20297 (designated PG777),
Vimentin (designated PG778),
Eukaryotic Translation Elongation Factor 2 (EEF2) (designated PG786),
Hypothetical Protein GI 14758649 (designated PG787),
Hypothetical Protein GI 11277141 (designated PG788),
Human Serine/Threonine Protein Phosphatase 2A (130 KDa regulatory subunit PP2A) (designated PG789), and
Hypothetical Protein GI 7705346 (designated PG790); and (b) selecting the triptolide or triptolide analog for said further testing of its ability to influence the activity of the target molecule based on the binding of the triptolide or triptolide analog to the target.

2. The method of claim 1, wherein the target molecule is 14-3-3 ε (designated PG773).

* * * * *